(12) United States Patent
Gejdos et al.

(10) Patent No.: US 8,315,989 B2
(45) Date of Patent: Nov. 20, 2012

(54) SYSTEM AND METHOD FOR DATABASE INTEGRITY CHECKING

(75) Inventors: Igor Gejdos, Indianapolis, IN (US); Lawrence G. Yarian, II, Auburn, IN (US); Keith E. Bernard, Fort Wayne, IN (US); Morris J. Young, Indianapolis, IN (US); Christopher R. Baker, Fishers, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/293,063

(22) Filed: Nov. 9, 2011

(65) Prior Publication Data

US 2012/0066185 A1    Mar. 15, 2012

Related U.S. Application Data

(63) Continuation of application No. 11/999,856, filed on Dec. 7, 2007, now Pat. No. 8,078,592.

(51) Int. Cl.
*G06F 7/00* (2006.01)
*G06F 17/00* (2006.01)

(52) U.S. Cl. ........................... 707/687; 707/690

(58) Field of Classification Search .................. None
See application file for complete search history.

(56) References Cited

U.S. PATENT DOCUMENTS

| | | | |
|---|---|---|---|
| 4,731,726 A | 3/1988 | Allen, III | |
| 5,251,126 A | 10/1993 | Kahn et al. | |
| 5,338,157 A | 8/1994 | Blomquist | |
| 5,376,070 A | 12/1994 | Purvis et al. | |
| 5,658,250 A | 8/1997 | Blomquist et al. | |
| 5,665,065 A | 9/1997 | Colman et al. | |
| 5,795,327 A | 8/1998 | Wilson et al. | |
| 5,954,641 A | 9/1999 | Kehr et al. | |
| 6,024,699 A | 2/2000 | Surwit et al. | |
| 6,068,615 A | 5/2000 | Brown et al. | |
| 6,102,855 A | 8/2000 | Kehr et al. | |
| 6,110,148 A | 8/2000 | Brown et al. | |
| 6,113,578 A | 9/2000 | Brown | |
| 6,241,704 B1 | 6/2001 | Peterson et al. | |
| 6,314,405 B1 | 11/2001 | Richardson | |
| 6,322,502 B1 | 11/2001 | Schoenberg et al. | |
| 6,368,272 B1 | 4/2002 | Porumbescu | |
| 6,427,088 B1 | 7/2002 | Bowman, IV et al. | |
| 6,544,212 B2 | 4/2003 | Galley et al. | |

(Continued)

FOREIGN PATENT DOCUMENTS

EP    0 699 046    9/1996

(Continued)

OTHER PUBLICATIONS

Roche Diagnostics, "Accu-Chek® Compass Diabetes Care Software", Users Guide, 2005, 74 pp., Roche Diagnostics Corp, listed as reference FL in the IDS dated May 19, 2009 and referred to hereinafter as Roche).*
Kim et al., "The Design and Implementation of Tripwire: A File System Integrity Checker", CCS '94, Nov. 1994, pp. 18-29, ACM.*
Cabri et al.; "Agent-based Plug-and-Play Integration of Role-Enabled Medical Devices", IEEE Computer Society, Aug. 2007, p. 111-121.

(Continued)

*Primary Examiner* — Michael Hicks
(74) *Attorney, Agent, or Firm* — Faegre Baker Daniels LLP (57) ABSTRACT

A method is disclosed for checking the integrity of a database through a test of database integrity information provided in the database and integrity information provided external to the database. The integrity information may be provided in a configuration file.

17 Claims, 9 Drawing Sheets

U.S. PATENT DOCUMENTS

| | | | |
|---|---|---|---|
| 6,551,276 | B1 | 4/2003 | Mann et al. |
| 6,558,320 | B1 | 5/2003 | Causey, III et al. |
| 6,562,001 | B2 | 5/2003 | Lebel et al. |
| 6,564,105 | B2 | 5/2003 | Starkweather et al. |
| 6,571,128 | B2 | 5/2003 | Lebel et al. |
| 6,577,899 | B2 | 6/2003 | Lebel et al. |
| 6,585,644 | B2 | 7/2003 | Lebel et al. |
| 6,605,038 | B1 | 8/2003 | Teller et al. |
| 6,635,014 | B2 | 10/2003 | Starkweather et al. |
| 6,648,821 | B2 | 11/2003 | Lebel et al. |
| 6,659,948 | B2 | 12/2003 | Lebel et al. |
| 6,668,196 | B1 | 12/2003 | Villegas et al. |
| 6,687,546 | B2 | 2/2004 | Lebel et al. |
| 6,694,191 | B2 | 2/2004 | Starkweather et al. |
| 6,714,724 | B1 | 3/2004 | Cook |
| 6,733,446 | B2 | 5/2004 | Lebel et al. |
| 6,740,075 | B2 | 5/2004 | Lebel et al. |
| 6,752,787 | B1 | 6/2004 | Causey, III et al. |
| 6,758,810 | B2 | 7/2004 | Lebel et al. |
| 6,781,522 | B2 | 8/2004 | Sleva et al. |
| 6,804,656 | B1 | 10/2004 | Rosenfeld et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,852,104 | B2 | 2/2005 | Blomquist |
| 6,873,268 | B2 | 3/2005 | Lebel et al. |
| 6,958,705 | B2 | 10/2005 | Lebel et al. |
| 7,020,508 | B2 | 3/2006 | Stivoric et al. |
| 7,024,236 | B2 | 4/2006 | Ford et al. |
| 7,029,455 | B2 | 4/2006 | Flaherty |
| 7,039,703 | B1 | 5/2006 | Clancy et al. |
| 7,041,468 | B2 | 5/2006 | Drucker et al. |
| 7,063,665 | B2 | 6/2006 | Hasegawa et al. |
| 7,072,356 | B1 | 7/2006 | Clancy et al. |
| 7,082,334 | B2 | 7/2006 | Boute et al. |
| 7,120,488 | B2 | 10/2006 | Nova et al. |
| 7,165,062 | B2 | 1/2007 | O'Rourke |
| 7,179,226 | B2 | 2/2007 | Crothall et al. |
| 7,181,350 | B2 | 2/2007 | Oberding et al. |
| 2002/0016568 | A1 | 2/2002 | Lebel et al. |
| 2002/0029776 | A1 | 3/2002 | Blomquist |
| 2002/0040208 | A1 | 4/2002 | Flaherty et al. |
| 2002/0193679 | A1 | 12/2002 | Malave et al. |
| 2003/0011646 | A1 | 1/2003 | Levine et al. |
| 2003/0060765 | A1 | 3/2003 | Campbell et al. |
| 2003/0065308 | A1 | 4/2003 | Lebel et al. |
| 2003/0065536 | A1 | 4/2003 | Hansen et al. |
| 2003/0163088 | A1 | 8/2003 | Blomquist |
| 2003/0163789 | A1 | 8/2003 | Blomquist |
| 2004/0073464 | A1 | 4/2004 | Huang |
| 2004/0119742 | A1 | 6/2004 | Silbey et al. |
| 2004/0172284 | A1 | 9/2004 | Sullivan et al. |
| 2004/0235446 | A1 | 11/2004 | Flaherty et al. |
| 2004/0254434 | A1 | 12/2004 | Goodnow et al. |
| 2004/0260233 | A1 | 12/2004 | Garibotto et al. |
| 2005/0004947 | A1 | 1/2005 | Emlet et al. |
| 2005/0022274 | A1 | 1/2005 | Campbell et al. |
| 2005/0137653 | A1 | 6/2005 | Friedman et al. |
| 2005/0192844 | A1 | 9/2005 | Esler et al. |
| 2006/0167367 | A1 | 7/2006 | Stanczak et al. |
| 2006/0248398 | A1 | 11/2006 | Neel et al. |
| 2006/0279431 | A1 | 12/2006 | Bakarania et al. |
| 2007/0033074 | A1 | 2/2007 | Nitzan et al. |
| 2007/0048691 | A1 | 3/2007 | Brown |
| 2007/0179352 | A1 | 8/2007 | Randlov et al. |
| 2007/0219432 | A1 | 9/2007 | Thompson |
| 2007/0276197 | A1 | 11/2007 | Harmon |

FOREIGN PATENT DOCUMENTS

| | | |
|---|---|---|
| EP | 0 970 655 | 1/2000 |
| EP | 0 649 316 B1 | 12/2000 |
| EP | 1 194 864 A2 | 4/2002 |
| EP | 1 502 614 | 2/2005 |
| EP | 1 722 310 | 4/2005 |
| WO | WO9728736 | 2/1997 |
| WO | WO9935856 | 12/1998 |
| WO | WO0018449 | 2/2000 |
| WO | WO0072181 | 11/2000 |
| WO | WO0200111 | 11/2000 |
| WO | WO02078512 | 10/2002 |
| WO | WO03015838 | 2/2003 |
| WO | WO2004090661 | 10/2004 |
| WO | WO2005011249 | 2/2005 |
| WO | WO2005037095 | 4/2005 |
| WO | WO2005096206 | 10/2005 |
| WO | WO2005114534 | 12/2005 |
| WO | WO2005114535 | 12/2005 |
| WO | WO2006050485 | 2/2006 |
| WO | WO2006108858 | 10/2006 |
| WO | WO2006118763 | 11/2006 |
| WO | WO2007051139 | 5/2007 |
| WO | WO2007093482 | 8/2007 |
| WO | WO2008147567 | 12/2008 |

OTHER PUBLICATIONS

"The HAVi Specification—Specification of the Home Audio/Video Interoperability (HAVi) Architecture," Nov. 19, 1998, pp. 1-409, Version 1.0 beta.

Hotchkiss et al.; "MD-Adapt a Proposed Architecture for Open-Source Medical Device Interoperability", 2007, IEEE Computer Society, Aug. 2007, pp. 167-169.

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

Roche Diagnostics, Accu-Chek® Compass Diabetes Care Software:, Users Guide, 2005, 74 pp., Roche Diagnostics Corp.

Aaslng, Jesper Mazanti, et al., Climate Control Software Integration with a Greenhouse Environmental Control Computer, Environmental Modeling and Software, Elsevier, Oxford, GB, vol. 20, No. 5, May 1, 2005.

Urban, Susan D., et al., "The Implementation and Evaluation of Integrity Maintenance Rules in an Object-Oriented Database", Data Engineering, 1992, Proceedings. Eight International Conference O N, Tempe, USA, IEEE Service Center, Los Alamitos, CA, vol. 12, No. 6.

Orman, L.V., "Transaction Repair for Integrity Enforcement", IEEE Transactions on Knowledge and Data Engineering, IEEE Service Center, Los Alamitos, CA, vol. 12, No. 6.

International Preliminary Search Report on Patentability for PCT/EP2008/009877 issued by the European Patent Office on Aug. 5, 2009.

* cited by examiner

SYSTEM AND METHOD FOR DATABASE INTEGRITY CHECKING

CROSS-REFERENCE TO RELATED APPLICATION

This application is a Continuation of U.S. patent application Ser. No. 11/999,856, filed Dec. 7, 2007, which is entitled SYSTEM AND METHOD FOR DATABASE INTEGRITY CHECKING, and published as U.S. Publication No. 2009-0150454 A1, the entire disclosure of which is expressly incorporated herein by reference.

FIELD OF THE INVENTION

The present invention relates generally to healthcare related database systems and in particular to integrity checks of healthcare related database systems.

BACKGROUND OF THE INVENTION

Databases are used to store patient physiological information, such as test data, in healthcare related database systems. This data is stored in respective units. For example, blood glucose (bG) values may be stored in milligrams per deciliter (mg/dL) or millimoles per liter (mmol/L). The significance of a value of 20 for blood glucose differs greatly depending on whether the units are mg/dL or mmol/L. Normal blood glucose values are generally in the range of about 4 mmol/L to about 8 mmol/L which is in the range of about 70 mg/dL to about 150 mg/dL. Returning to the value of 20, at 20 mg/dL the patient is well under the normal range while at 20 mmol/L the patient is well above the normal range. As is known, a caregiver or patient may make different therapy or lifestyle choices based on whether the value of the patient's blood sugar is above normal or below normal.

Regardless of the units in which the data is stored, the data may be presented to a user in another unit. For instance, the blood glucose values of the patient may be stored in the database in the units mg/dL and a user of a software package accessing the database may desire to have the patient blood glucose values displayed on a report in mmol/L. As is known, a conversion may be made to convert from mmol/L to mg/dL, as illustrated by equation 1.

$$bG \text{ (mmol/L)} * n = bG \text{ (mg/dL)} \quad (1)$$

In equation 1, n is a conversion factor. For equation 1, n is equal to about 18. As stated above, a caregiver or patient may make different therapy or lifestyle choices based on whether the value of the patient's blood sugar is above normal or below normal. As such, the value of n needs to be accurate to reflect the correct values of a patient's blood glucose to a caregiver or patient when displayed or otherwise presented in a unit different from the unit that the value is stored.

Although the exemplary blood glucose conversion given above has a single conversion factor, other conversions have multiple conversion quantities, such as converting temperature from Celsius scale to Fahrenheit scale which has both a conversion factor and a conversion offset.

SUMMARY OF THE INVENTION

The present invention relates generally to healthcare related database systems and in particular to integrity checks of healthcare related database systems. A healthcare management software system is provided. The healthcare management software system includes the ability to review physiological information about one or more patients.

In an exemplary embodiment of the present disclosure, a method of checking the integrity of a database containing both physiological information and database integrity information is provided. The database being accessible by a healthcare management software system. The method including the steps of storing integrity information on a computer readable media accessible by the healthcare management software system, the integrity information being stored separate from the database; and determining an integrity of the database based on a test of the integrity information and the database integrity information contained in the database.

In another exemplary embodiment of the present disclosure, a method of checking the integrity of a database containing both physiological information and database integrity information is provided. The database being accessible by a healthcare management software system. The method including the step of providing a computer readable medium including an installation software which installs a version of a healthcare management software system. The installation software being able to perform at least a first installation of a first version of the healthcare management software system including a first database having a first database integrity information and a first file containing a first integrity information and a second installation of a second version of the healthcare management software system including a second database having a second database integrity information and a second file containing a second integrity information. The method further including the steps of receiving a request to perform the first installation; installing the first version of the healthcare management software system; and determining an integrity of the first database through a test of the first database integrity information with the first integrity information.

In a further exemplary embodiment of the present disclosure, a system for managing healthcare related information is provided. The system including at least a first computing device; and a memory accessible by the first computing device. The memory including healthcare management software system including instructions to display on a display a user interface of the healthcare management software system, instructions to display on the display representations of physiological information included in a patient database accessible by the healthcare management software system, and a file including integrity information. The healthcare management software system including instructions to verify an integrity of the patient database through a test of a database integrity information contained in the patient database with the integrity information.

In yet another exemplary embodiment of the present disclosure, a user interface of a healthcare management software system to be presented on an electronic display is provided. The healthcare management software system having access to a database containing physiological information. The user interface comprising: a first selection input to request a check of the integrity of the database containing physiological information; and a second selection input to download additional physiological information from a remote device, the additional physiological information being included in the database.

In still a further exemplary embodiment of the present disclosure, a computer readable medium having computer-executable instructions for checking the integrity of a database containing both physiological information and database integrity information is provided. The computer executable instructions including instructions to display a user interface of a healthcare management software system; and instructions to determine an integrity of the database based on a test of integrity information stored external to the database and the database integrity information contained in the database.

In still another exemplary embodiment of the present disclosure, a computer readable medium having computer-executable instructions is provided. The computer executable instructions including an installation software which installs a version of a healthcare management software system. The installation software being able to perform at least a first installation of a first version of the healthcare management software system including a first database having a first database integrity information and a first file containing a first integrity information and a second installation of a second version of the healthcare management software system including a second database having a second database integrity information and a second file containing a second integrity information.

Additional features and advantages of the present invention will become apparent to those skilled in the art upon consideration of the following detailed description of illustrative embodiments exemplifying the best mode of carrying out the invention as presently perceived.

BRIEF DESCRIPTION OF DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to the precise forms disclosed. Rather, the embodiments selected for description have been chosen to enable one skilled in the art to practice the invention.

Concepts described herein may be further explained in one of more of the co-filed patent applications entitled HELP UTILITY FUNCTIONALITY AND ARCHITECTURE 11/999,906, METHOD AND SYSTEM FOR GRAPHICALLY INDICATING MULTIPLE DATA VALUES 11/999,853, METHOD AND SYSTEM FOR DATA SOURCE AND MODIFICATION TRACKING 11/999,888, PATIENT-CENTRIC HEALTHCARE INFORMATION MAINTENANCE 11/999,874, EXPORT FILE FORMAT WITH MANIFEST FOR ENHANCED DATA TRANSFER 11/999,867, GRAPHIC ZOOM FUNCTIONALITY FOR A CUSTOM REPORT 11/999,932, METHOD AND SYSTEM FOR SELECTIVE MERGING OF PATIENT DATA 11/999,859, METHOD AND SYSTEM FOR PERSONAL MEDICAL DATA DATABASE MERGING 11/999,772, METHOD AND SYSTEM FOR WIRELESS DEVICE COMMUNICATION 11/999,879, METHOD AND SYSTEM FOR SETTING TIME BLOCKS (11/999,868, METHOD AND SYSTEM FOR ENHANCED DATA TRANSFER 11/999,911, COMMON EXTENSIBLE DATA EXCHANGE FORMAT 11/999,871, METHOD OF CLONING SERVER INSTALLATION TO A NETWORK CLIENT 11/999,876,METHOD AND SYSTEM FOR QUERYING A DATABASE 11/999,912, METHOD AND SYSTEM FOR EVENT BASED DATA COMPARISON 11/999,921, DYNAMIC COMMUNICATION STACK 11/999,934,SYSTEM AND METHOD FOR REPORTING MEDICAL INFORMATION 11/999,878, METHOD AND SYSTEM FOR MERGING EXTENSIBLE DATA INTO A DATABASE USING GLOBALLY UNIQUE IDENTIFIERS 11/999,947, METHOD AND SYSTEM FOR ACTIVATING FEATURES AND FUNCTIONS OF A CONSOLIDATED SOFTWARE APPLICATION 11/999,880,METHOD AND SYSTEM FOR CONFIGURING A CONSOLIDATED SOFTWARE APPLICATION 11/999,894, METHOD AND SYSTEM FOR DATA SELECTION AND DISPLAY 11/999,896,METHOD AND SYSTEM FOR ASSOCIATING DATABASE CONTENT FOR SECURITY ENHANCEMENT 11/999,951, METHOD AND SYSTEM FOR CREATING REPORTS 11/999,851, METHOD AND SYSTEM FOR CREATING USER-DEFINED OUTPUTS 11/999,905, DATA DRIVEN COMMUNICATION PROTOCOL GRAMMAR 11/999,770, HEALTHCARE MANAGEMENT SYSTEM HAVING IMPROVED PRINTING OF DISPLAY SCREEN INFORMATION 11/999,855, and METHOD AND SYSTEM FOR MULTI-DEVICE COMMUNICATION 11/999,866, the entire disclosures of which are hereby expressly incorporated herein by reference. It should be understood that the concepts described herein may relate to diabetes management software systems for tracking and analyzing health data, such as, for example, the ACCU-CHEK®360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics or divisions thereof.

Figure 1:
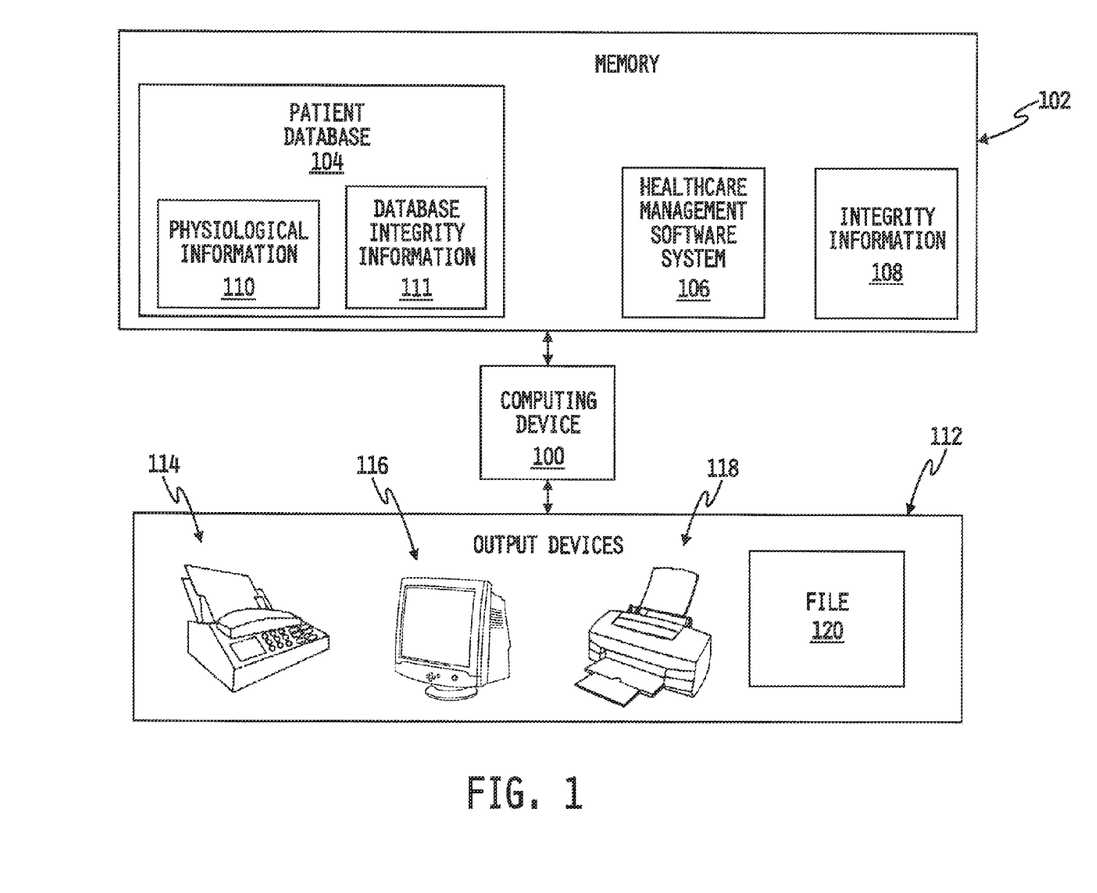
FIG. 1 is a representation of a computing device having access to one or more output devices and access to a memory containing a patient database, a healthcare management software system, and integrity information.

Referring to FIG. 1, a computing device 100 is shown. Computing device 100 may be a general purpose computer or a portable computing device. Although computing device 100 is illustrated as a single computing device, it should be understood that multiple computing devices may be used together, such as over a network or other methods of transferring data. Exemplary computing devices include desktop computers, laptop computers, personal data assistants ("PDA"), such as BLACKBERRY brand devices, cellular devices, tablet computers, infusion pumps, blood glucose meters, or an integrated device including a glucose measurement engine and a PDA or cell phone.

Computing device 100 has access to a memory 102. Memory 102 is a computer readable medium and may be a single storage device or multiple storage devices, located either locally with computing device 100 or accessible across a network. Computer-readable media may be any available media that can be accessed by the computer 102 and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store the desired information and which can be accessed by the computing device 100.

Memory 102 includes one or more patient databases 104, healthcare management software system 106, and integrity information 108. Patient databases 104 include physiological information 110 related to one or more patients. Exemplary physiological information includes blood glucose values, A1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, and weight values. Physiological information 110 may be provided directly by the patient, provided by a caregiver, and/or provided by one or more sensors. Exemplary sensors are provided in insulin pumps and glucose meters.

Healthcare management software system 106 includes instructions which when executed by computing device 100 present physiological information 110 or information based on physiological information 110 to an output device 112. Exemplary information presented by healthcare management software system 106 to output device 112 include diaries of blood glucose values and reports showing a plurality of blood glucose values. Exemplary reports include standard day reports wherein the blood glucose values are grouped according to the time of day taken, standard week reports wherein the blood glucose values are grouped according to the day of the week taken, trend graphs to illustrate temporal trends in blood glucose values, and other suitable reports.

Computing device 100 has access to output device 112. Exemplary output devices 112 include fax machines 114, displays 116, printers 118, and files 120. Files 120 may have various formats. In one embodiment, files 120 are portable document format (PDF) files. In one embodiment, files 120 are formatted for display by an Internet browser, such as internet Explorer available from Microsoft of Redmond, Wash., and may include one or more of HyperText Markup Language ("HTML"), or other formatting instructions. In one embodiment, files 120 are files stored in memory 102 for transmission to another computing device and eventual presentation by another output device or to at least influence information provided by the another output device.

Memory 102 further includes integrity information 108. Integrity information 108 is information contained separate from patient database 104 which provides a check of the data in patient database 104 to ensure that the physiological information 110 or information based on physiological information 110 is presented to output device 112 by healthcare management software system 106 correctly. As mentioned herein, physiological information 110 may be used by patients and/or healthcare professionals to determine therapy adjustments for the patient and/or lifestyle adjustments for the patient. Exemplary therapies include insulin and other medications.

Integrity information 108 differs from security information. Traditionally security information has been used in software systems to ensure that a given user has permission to access physiological information 110 and/or to ensure that a license associated with the software is other than past due. Integrity information 108 is not associated with these traditional functions of security information. That said, in one embodiment, integrity information 108 may be included in the same file as security information.

Integrity information 108 is defined as information which is used to verify the accuracy of the database, such as patient database 104. Integrity information 108 may include both data used in determining information to present with output device 112 and data not used in determining information to present with output device 112. Exemplary information used in determining information to present with output device 112 includes conversion quantities, units, textual labels, and other information presented with output device 112 or used to determine information presented with output device 112. Exemplary information not used in determining information to present with output device 112 includes keys, identification information, and other suitable information.

In one embodiment, integrity information 108 is a part of a configuration file 140 stored in memory 102. In one embodiment, configuration file 140 is an encrypted file. Known encryption techniques may be used to encrypt configuration file 140. An exemplary encryption technique is to determine a digest of configuration file 140 and then encrypt with a private key. This produces a signed encrypted configuration file 140. In one embodiment, configuration file 140 is not an encrypted file. In one embodiment, wherein configuration file 140 is unencrypted an assurance of the contents of configuration file 140 may be made through other ways, such as whether the configuration file is stored on a read only media or a checksum.

Figure 2:
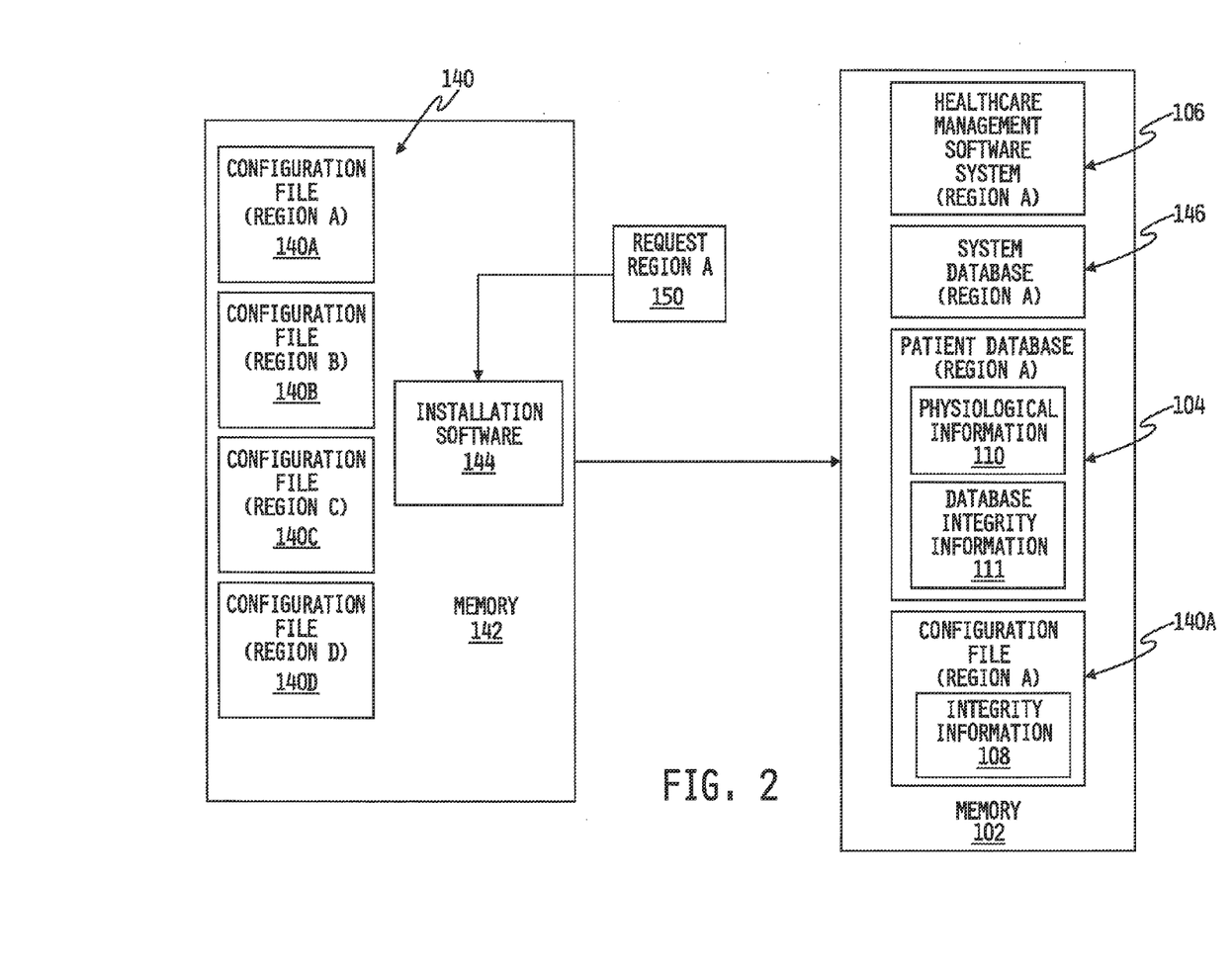
FIG. 2 is a representation of an installation software provided on a memory and an installed version of a healthcare management software system installed on a second memory in response to a request.

Referring to FIG. 2, in one embodiment, a computer readable media 142 is provided that includes installation software 144 which installs healthcare management software system 106 on memory 102 which is accessible by computing device 100. Computer readable media 142 also includes a plurality of configuration files 140, illustratively configuration files 140A-D. Each of configuration files 140A-D corresponds to a particular version of healthcare management software system 106 which may be installed. In the illustrated example, each of configuration files 140A-D corresponds to a particular region for which the healthcare management software system 106 may be configured. Exemplary regions include, the United States (US), Canada (CA), Germany (DE), and the remainder of the world (OTHER).

In one embodiment, installation software 144 receives a request 150 to install a version of healthcare management software system 106 which is configured for region A on computer readable media 102. Request 150 may be provided by an operator through a selection made during execution of installation software 144. Request 150 may be provided as a portion of an activation key provided by an operator during execution of installation software 144.

During installation of healthcare management software system 106 for region A, installation software 144 places on computer readable media 102 a system database 146, a patient database 104, and configuration file 140A. System database 146 includes information regarding the user's of healthcare management software system 106 and setting information. Exemplary setting information includes user access information, user specific and system wide setting information, such as customized appearance of the system and customized report settings. Patient database 104 includes physiological information 110 and database integrity information 111. Database integrity information is the information contained in database 104 which is tested against integrity information 108 to determine the integrity of database 104. Configuration file 140A includes integrity information 108.

Figure 3:
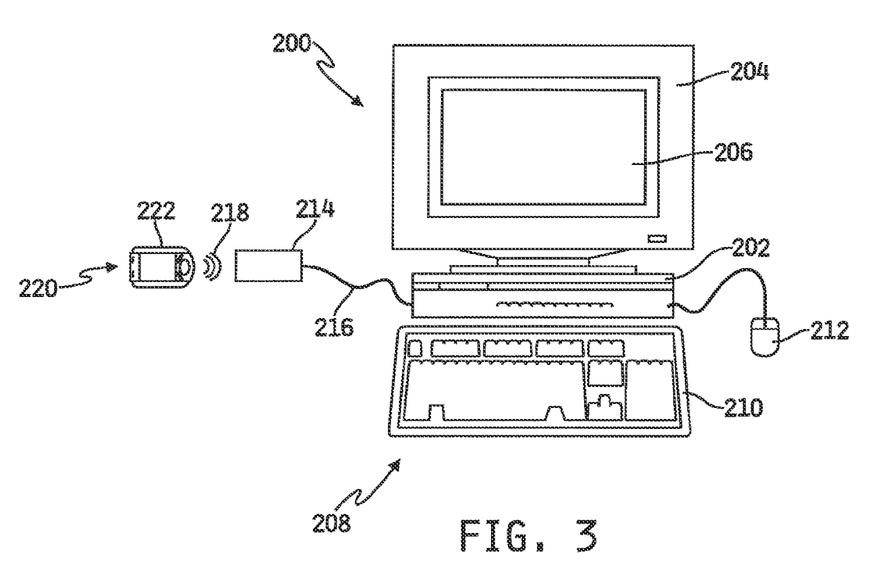
FIG. 3 is a representation of an exemplary computing device receiving information from a remote medical device.

In one embodiment, healthcare management software system 106 is diabetes care software which is loaded on a computing device 100. The diabetes care software interacts with a blood glucose meter to receive blood glucose values and other physiological information. The diabetes care software system then is able to present the blood glucose values to the patient or caregiver for review. Referring to FIG. 3, an exemplary computing device 200 is shown. In one embodiment, installation software 144 installs a diabetes care software system on computing device 200 as described above. Computing device 200 is a personal computer 202. Computing device 200 is coupled to an output device 204, illustratively a display screen 206. Computing device 200 is further coupled to a plurality of input devices 208. A first exemplary input device is a keyboard 210. A second exemplary input device is a mouse 212. A third exemplary input device is a modulated signal transceiver 214, in electronic communication with computer 202 through a cable 216. Transceiver 214 is configured to transmit and receive a modulated signal 218 and to establish communications to and from a remote device 220. An exemplary remote device 220 is a blood glucose meter 222.

In one embodiment, blood glucose meter 222 is assigned to a patient and associated with that patient in healthcare management software system 106. Thus, when physiological information from blood glucose meter 222 is transferred to healthcare management software system 106, the physiological information from blood glucose meter 222 automatically populates database records in patient database 104 relating to that patient.

Although a blood glucose meter 222 is shown, any medical device may be implemented having data to be used by healthcare management software system 106. Medical devices 220 are devices capable of recording patient data and transferring data to software applications and may include monitors which record values of measurements relating to a patient's state and information such as the time and date when the measurement was recorded. Medical devices may also be devices configured to provide medications to patients such as, for example, insulin pumps. These devices, generally, record dosage amounts as well as the time and date when the medication was provided. It should be understood that the functionality of medical device 220 may be included within an exemplary computing device 100.

Computing device 200 may be used by the patient, a caregiver, or anyone having relevant data pertaining to a patient. Computing device 200 may be located in a patient's home, a healthcare facility, a drugstore, a kiosk, or any other convenient place. In an alternative embodiment, computing device 200 may be connected to a remote computing device, such as at a caregiver's facility or a location accessible by a caregiver, and physiological information 110 in patient database 104, or the complete patient database 104, may be transferred between them. In this embodiment, computing device 200 and the remote device are configured to transfer physiological information 110 in patient database 104, or the complete patient database 104, between them through a data connection such as, for example, via the Internet, cellular communications, or the physical transfer of a memory device such as a diskette, USB key, compact disc, or other portable memory device. Computing device 200 and/or the remote device, may be configured to receive physiological information 110 from a medical device or, alternatively, to receive physiological information 110 transferred from the other of computing device 200 and the remote device.

Figure 4:
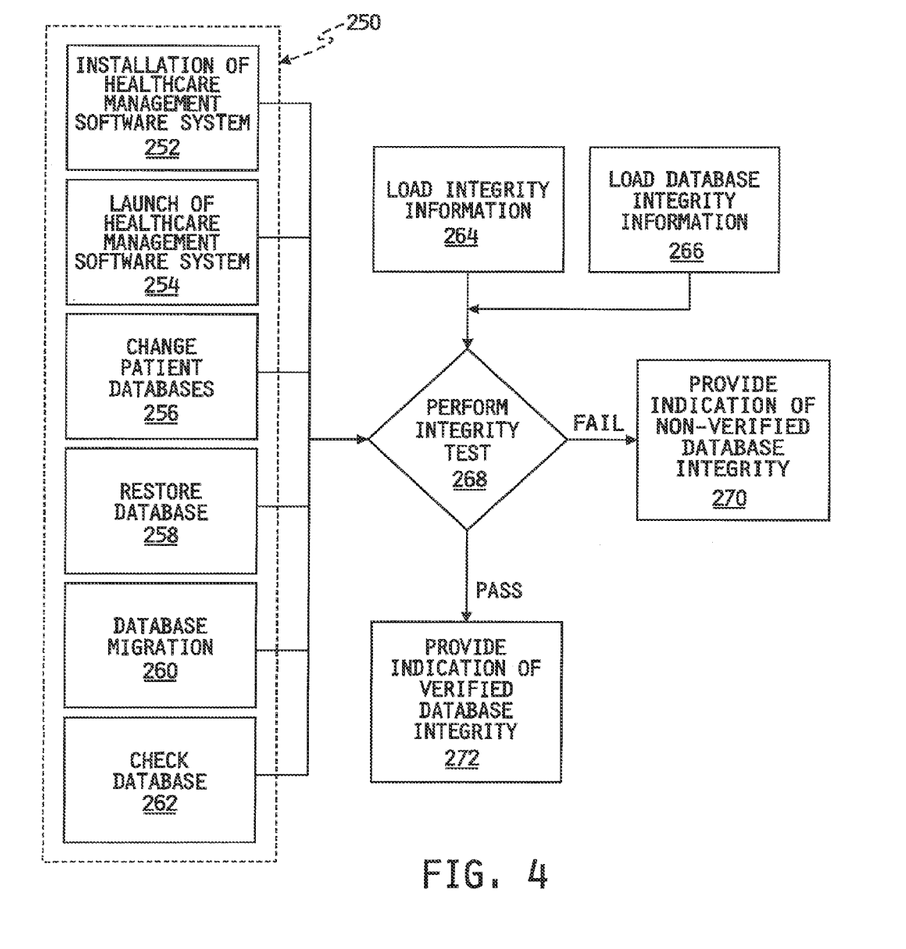
FIG. 4 is a representation of the checking of an integrity of a database in response to one of a plurality of conditions.

Referring to FIG. 4, healthcare management software system 106 performs an integrity check of patient database 104. Six exemplary conditions 250 are shown which result in the performance of an integrity check of patient database 104. A first exemplary condition 252 is upon the installation of the healthcare management software system 106. Once the healthcare management software system 106 is installed it performs a check of the integrity of the patient database 104 created during the installation. A second exemplary condition 254 is upon a launch of the healthcare management software system 106 by computing device 100. A launch of healthcare management software system 106 may occur in response to a user requesting a launch, such as by selecting an icon on display 116. A launch of healthcare management software system 106 may occur in response to the detection of a blood glucose meter 222 by computing device 200. A third exemplary condition 256 is upon the associating of a different patient database 104 with healthcare management software system 106. A fourth exemplary condition 258 is upon a request to restore a patient database 104. A fifth exemplary condition 260 is upon a request to migrate information from a different format to a patient database 104. An exemplary different format is a patient database for another healthcare monitoring software system, such as the Accu-Chek Compass software system available from the assignee of the present application. A sixth exemplary condition 262 is upon a request from a user to check the integrity of the patient database 104.

To check the integrity of the patient database 104, healthcare management software system 106 loads the integrity information 108 and the database integrity information 111, as represented by blocks 264 and 266. The healthcare management software system 106 then performs an integrity test of the patient database 104, as represented by block 268. The integrity test may be any process whereby the accuracy of patient database 104 may be affirmed or denied. An exemplary integrity test is provided in FIG. 5 and explained below. The healthcare management software system 106 provides an indication of a non-verified database integrity in response to a failed integrity test, as represented by block 270. An exemplary indication of a non-verified database integrity test is an error message presented by one of output devices 112. The healthcare management software system 106 provides an indication of a verified database integrity in response to a passed integrity test, as represented by block 272. An exemplary indication of a verified database integrity test is a message presented by one of output devices 112. Another exemplary indication of a verified database integrity test is the launching of the healthcare management software system 106.

Figure 5:
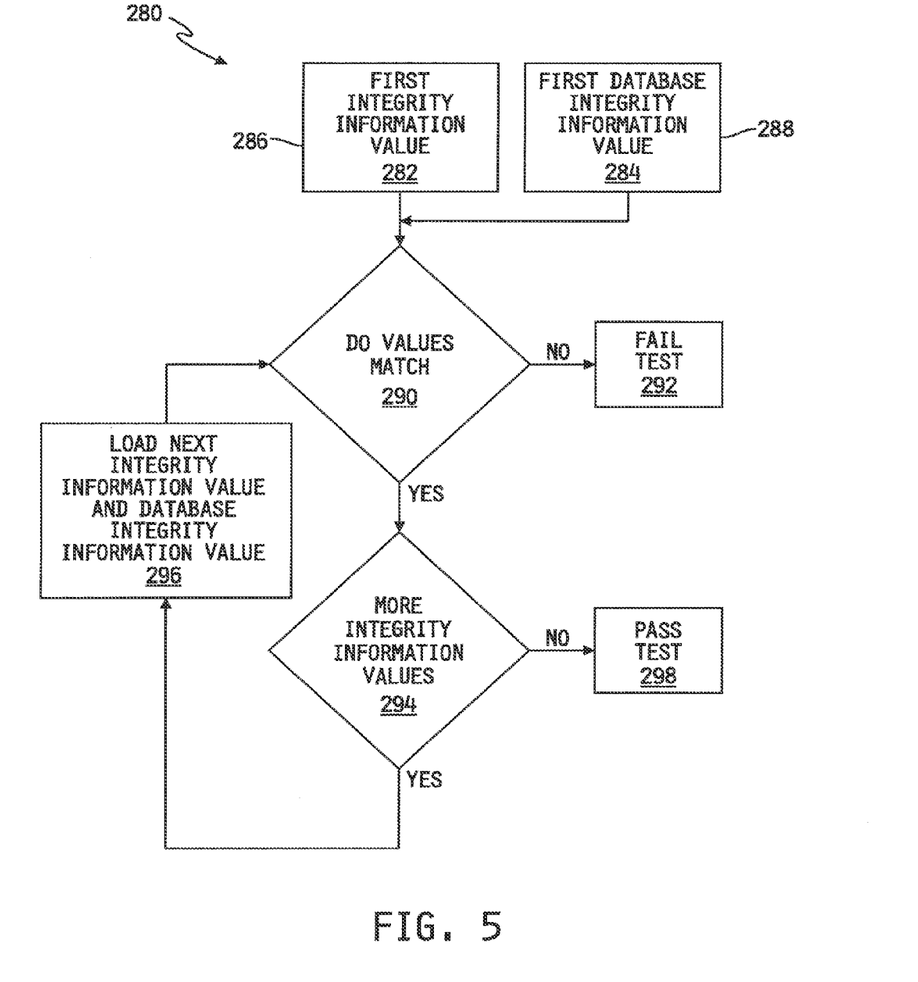
FIG. 5 is a representation of an exemplary method of checking the integrity of a database.

Referring to FIG. 5, an exemplary integrity test 280 is represented. Healthcare management software system 106 loads a first integrity information value 282 and a first database integrity information value 284, as represented by blocks 286 and 288, respectively. Healthcare management software system 106 compares the first integrity information value 282 and the first database integrity information value 284, as represented by block 290. If the first integrity information value 282 and the first database integrity information value 284 do not match, then the integrity test 280 fails, as represented by block 292. If the first integrity information value 282 and the first database integrity information value 284 match, a check is made whether additional integrity values still need to be checked, as represented by block 294. If additional integrity values are present, the next integrity information value 282 and database integrity information value 284 are loaded by healthcare management software system 106, as represented by block 296 and the comparison of the new values is performed, as represented by block 290. This repeats until either the integrity test fails or there are not any additional integrity information values 282 and database integrity information values 284 to check. At the point that there are not any additional integrity information values 282 and database integrity information values 284 to check, the integrity test passes, as represented by block 298.

Exemplary information for integrity information 108 and database integrity information 111 include conversion quantities, default units for display, default low and high data targets, and lists of insulin. Exemplary information for integrity information 108 and database integrity information 111 are provided in the following table:

| Data Type | Units | Storage Unit | Default Display unit | Conversion factor | Conversion offset |
| --- | --- | --- | --- | --- | --- |
| A1c | % | Y | Y | 1 | 0 |
| Albumin | mg/L | Y | Y | 1 | 0 |
| Albumin excretion | micrograms/min | Y | Y | 1 | 0 |
| Albumin excretion | mg/day | N | N | 1.44 | 0 |
| bG (meter) | mg/dL | Y | Y | 1 | 0 |
| bG (meter) | mmol/L | N | N | 0.0555 | 0 |
| bG (Laboratory) | mg/dL | Y | Y | 1 | 0 |
| bG (Laboratory) | mmol/L | N | N | 0.0555 | 0 |
| BMI | kg/m$^2$ | Y | Y | 1 | 0 |
| Blood pressure (diastolic) | kPa | Y | N | 1 | 0 |
| Blood pressure (diastolic) | mmHg | N | Y | 7.5002 | 0 |
| Blood pressure (systolic) | kPa | Y | N | 1 | 0 |
| Blood pressure (systolic) | mmHg | N | Y | 7.5002 | 0 |
| Carbohydrates | g | Y | Y | 1 | 0 |
| Carbohydrates | BE | N | N | 0.0833 | 0 |
| Carbohydrates | CE (1:15) | N | N | 0.0667 | 0 |
| Carbohydrates | CE (1:20) | N | N | 0.05 | 0 |
| Carbohydrates | CE (1:12) | N | N | 0.0833 | 0 |
| Carbohydrates | BW | N | N | 0.1 | 0 |
| Carbohydrates | CB | N | N | 0.0667 | 0 |
| Carbohydrates | KE | N | N | 0.1 | 0 |
| Carbohydrates | PTGL | N | N | 0.05 | 0 |
| Cholesterol (Total) | mg/dL | Y | Y | 1 | 0 |
| Cholesterol (Total) | mmol/L | N | N | 0.0259 | 0 |
| Cholesterol (HDL) | mg/dL | Y | Y | 1 | 0 |
| Cholesterol (HDL) | mmol/L | N | N | 0.0259 | 0 |
| Cholesterol (LDL) | mg/dL | Y | Y | 1 | 0 |
| Cholesterol (LDL) | mmol/L | N | N | 0.0259 | 0 |
| Cholesterol (Ratio) | NULL | Y | Y | 1 | 0 |
| Creatinine | micromol/L | Y | Y | 1 | 0 |
| Creatinine | mg/dL | N | N | 0.0113 | 0 |
| Fructosamine | micromol/L | Y | Y | 1 | 0 |
| Fructosamine | mg/dL | N | N | 0.179 | 0 |
| HbA1 | % | Y | Y | 1 | 0 |
| Height | cm | Y | N | 1 | 0 |
| Height | inches | N | Y | 0.3937 | 0 |
| Insulin Dose (Bolus) | units | Y | Y | 1 | 0 |
| Insulin Rate | units/hour | Y | Y | 1 | 0 |
| Total Daily Insulin Dose | units | Y | Y | 1 | 0 |
| Microalbumin | micrograms/dL | Y | Y | 1 | 0 |
| Proteinuria | mg/dL | Y | Y | 1 | 0 |
| Heart Rate | bpm | Y | Y | 1 | 0 |
| Relative Factor | % | Y | Y | 1 | 0 |
| Temperature | ° C. | Y | N | 1 | 0 |
| Temperature | ° F. | N | Y | 1.8 | −32 |
| Triglycerides | mg/dL | Y | Y | 1 | 0 |
| Triglycerides | mmol/L | N | N | 0.0114 | 0 |
| Weight | kg | Y | N | 1 | 0 |
| Weight | lbs | N | Y | 2.2002 | 0 |

Integrity information 108 and database integrity information 111 may be any of the values listed in columns 2-6 for database attributes given in the left-most column, column 1. Of course, the values in the table may differ depending on the version of healthcare management software system 106 installed. For example, for the weight attribute the default displayed unit may be kilograms for a version for Europe while it is pounds for a version for the United States. Therefore, the integrity information 108 and database integrity information 111 may differ for different versions of healthcare management software system 106. In one embodiment, both integrity information 108 and database integrity information 111 have the exact same values.

Figure 6:
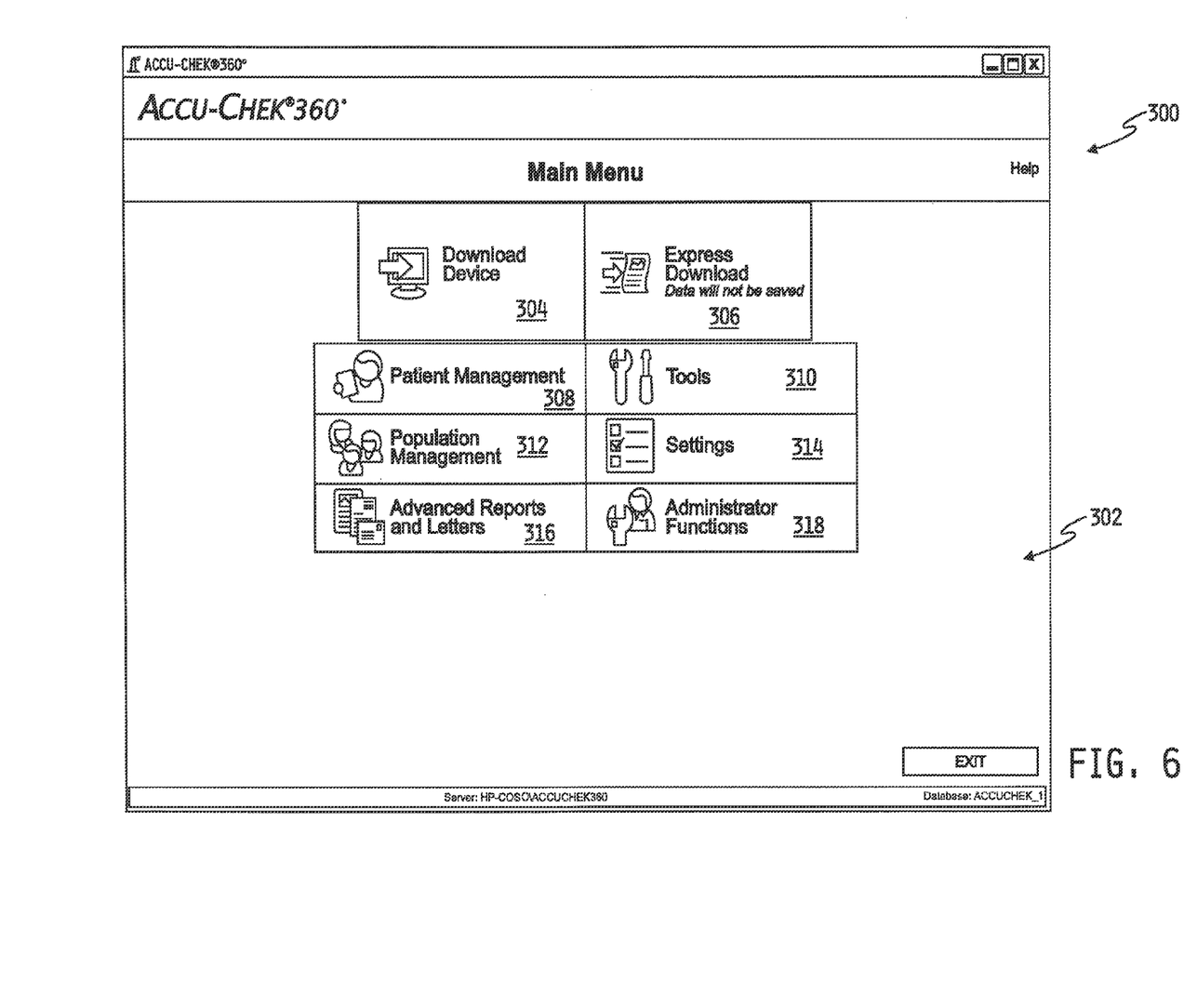
FIG. 6 is an exemplary main menu screen of a user interface of a healthcare management software system.
Figure 7:
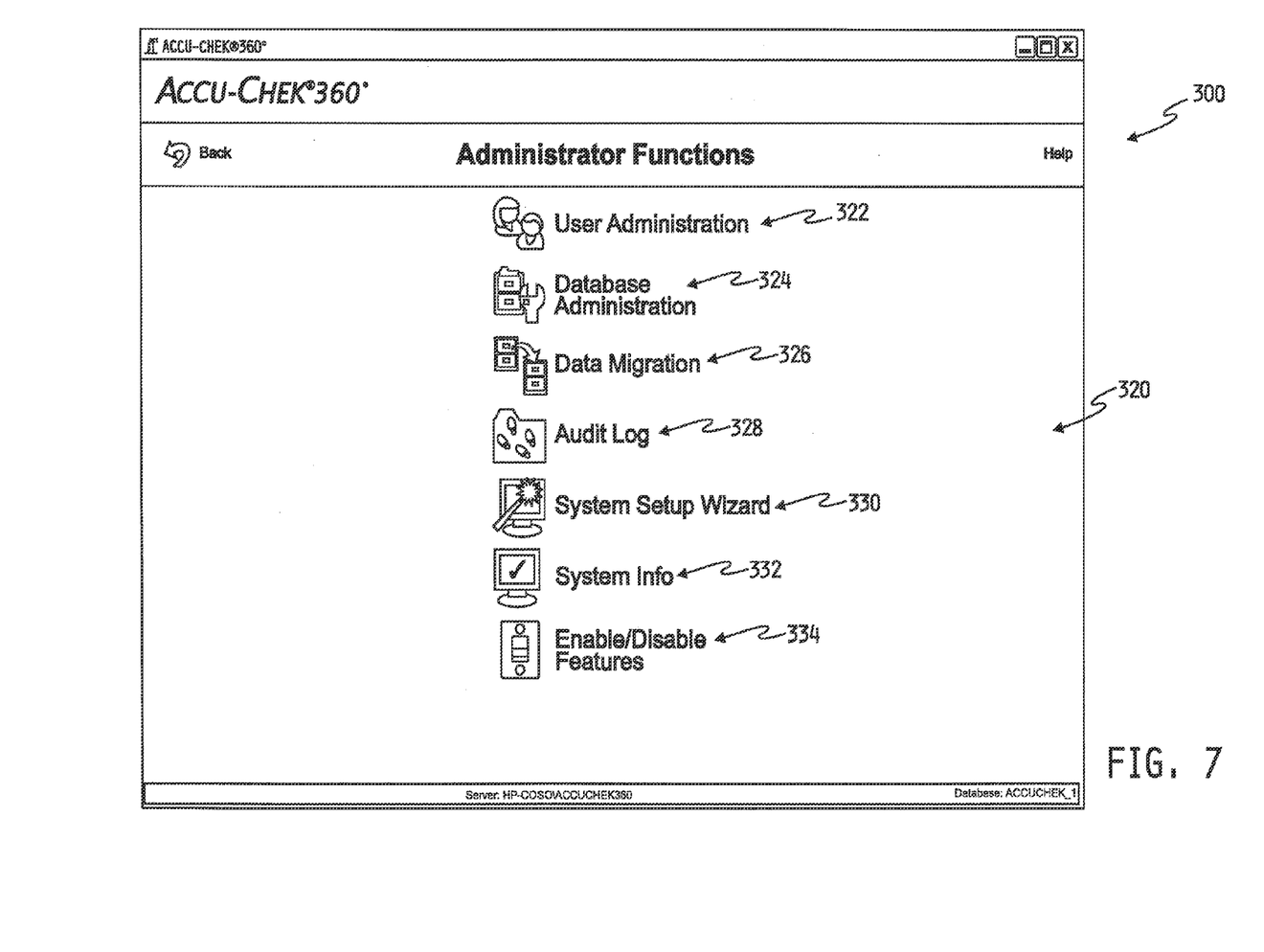
FIG. 7 is an exemplary administrator functions screen of a user interface of a healthcare management software system.
Figure 8:
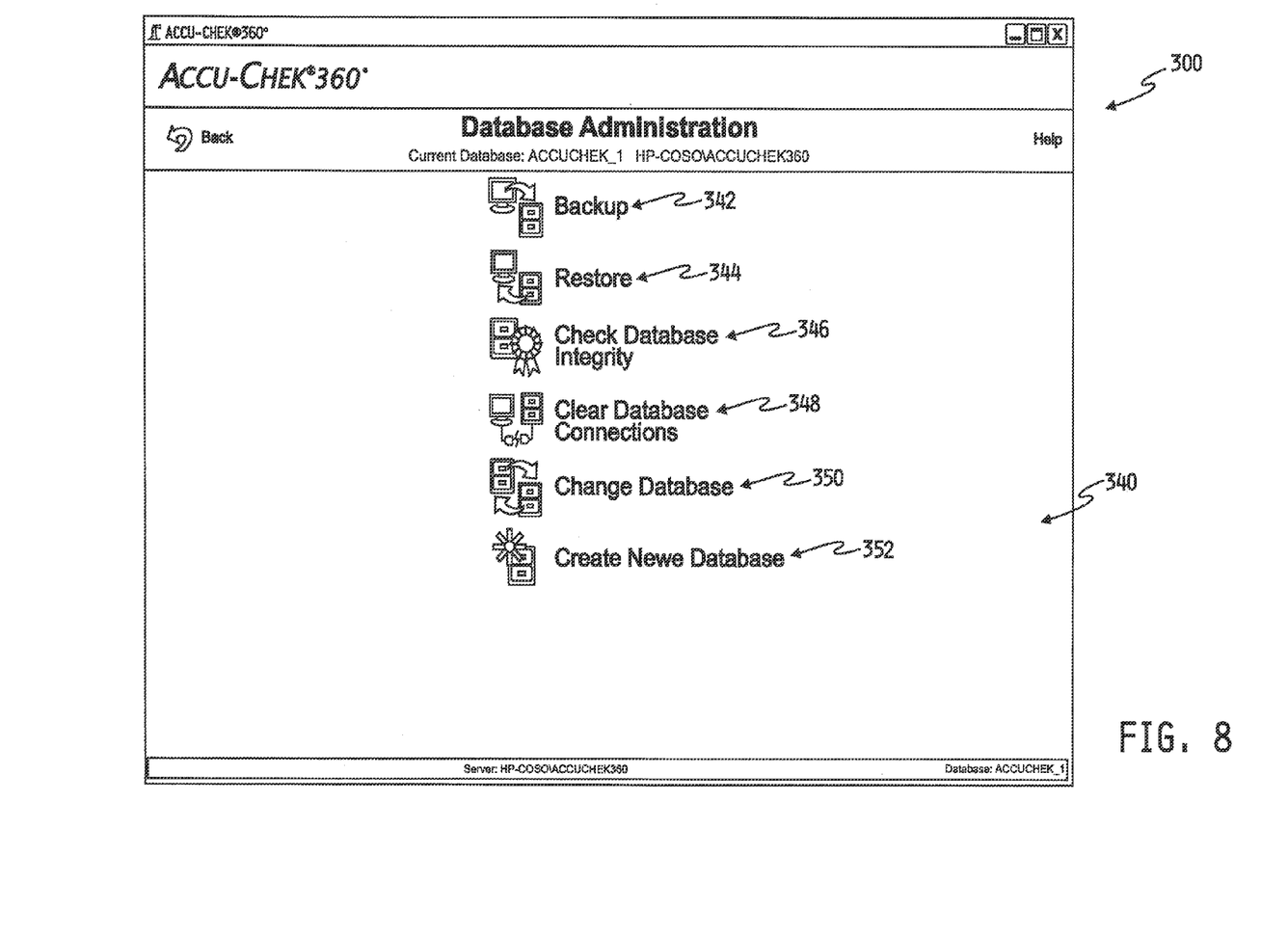
FIG. 8 is an exemplary database administration screen of a user interface of a healthcare management software system.

An embodiment of healthcare management software system 106 is shown in FIGS. 6-9. User interface 300 is shown. Referring to FIG. 6, a main menu screen 302 of user interface 300 is shown. Screen 302 includes a first selection input 304 for downloading physiological information 110 from glucose meter 222 for inclusion in patient database 104. A second selection input 306 is provided for downloading physiological information 110 from glucose meter 222, but not for storing in patient database 104. A third selection input 308 is provided for managing physiological information 110 in patient database 104 including generation of reports and entry of additional physiological information 110.

A fourth selection input 310 is provided for a tools menu. The tools menu includes selection inputs for importing physiological information 110, exporting physiological information 110, clearing physiological information 110 on a meter 222 in communication with healthcare management software system 106, setting the date and time of a meter 222 in communication with healthcare management software system 106, determining by brand the amount of testing data communicated from a plurality of meters 222. As such, a caregiver may see that for meter brand A 3000 entries of testing data for 20 patients were downloaded while for meter brand B 1000 entries of testing data for 20 patients were downloaded. The caregiver may then have a clearer picture of the brand of meter that their patients are using more frequently.

A fifth selection input 312 is provided for population management. Exemplary population management includes the ability to create groups based on either query groups where the database is queried to find patients that satisfy a criteria or a static group query. An exemplary static query group is a drug effectiveness group. The patients included in the drug effectiveness group are known and should not be allowed to change based on a query criteria. A sixth selection input 314 is provided for changing the settings of healthcare management software system 106. A seventh selection input 316 is provided for advanced reports and letters which allows a user to create custom reports through a report template builder and a letter builder which generates letters to patients in the database meeting a given criteria. Exemplary criteria include recent office visit, upcoming testing, and other criteria. A eighth selection input 318 is provided for administrator functions.

Upon selection of the eighth selection input 318, screen 320 (see FIG. 7) is presented on user interface 300. A first selection input 322 is provided for user administration. Exemplary user administration functions include creating a new user in healthcare management software system 106, deleting a user from healthcare management software system 106, and changing the role (administrator or not) of a user in healthcare management software system 106. A second selection input 324 is provided for database administration. Exemplary database administration functions are discussed in connection with FIG. 8 below. A third selection input 326 is provided for data migration. Data migration copies physiological information 110 from a database for another healthcare management software system. A fourth selection input 328 is provided for an audit log. Exemplary audit log functions include the either printing or viewing an audit log for a designated date range to show records of usage. A fifth selection input 330 is provided for a system setup wizard. Exemplary system setup wizard functions include the ability to define default settings for an installation of healthcare management software system 106. A sixth selection input 332 is provided for system information which provides a pop-up window including both healthcare management software system 106 information (such as version) and information regarding computing device 100 and peripherals (such as operating system, service packs installed, type of cable 216 connecting meter 222 to computing device 200, and the type of processor of computing device 200). A seventh selection input 334 is provided for enable/disable functions which allows a user to enable or disable features of healthcare management software system 106.

Upon selection of the second selection input 324, screen 340 (see FIG. 8) is presented on user interface 300. A first selection input 342 is provided for database backup wherein a copy of patient database 104 is stored. A second selection input 344 is provided for database restore wherein the information in patient database 104 is restored from a previous backup copy of patient database 104. A third selection input 346 is provided for check database integrity wherein an integrity test is performed on patient database 104. A fourth selection input 348 is provided for clearing database connections wherein all connections by other users to patient database 104 are cleared. A fifth selection input 350 is provided for changing databases wherein another patient database 104 may be loaded. A sixth selection input 352 is provided for creating a new patient database 104.

Figure 9:
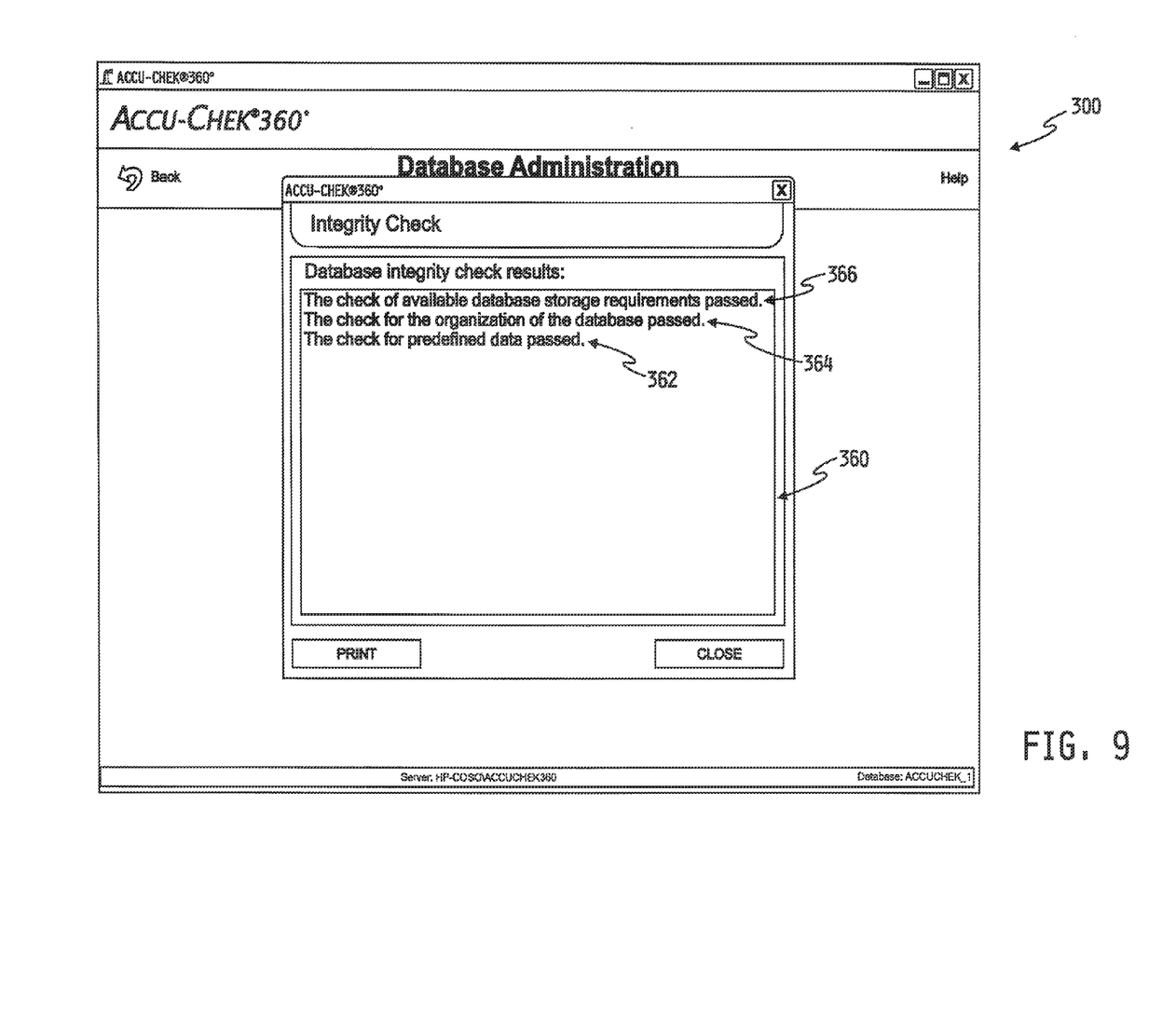
FIG. 9 is an exemplary pop-up window of a user interface of a healthcare management software system providing an indication that a database passed an integrity check.

Healthcare management software system 106, upon selection of selection input 346, performs an integrity test of the patient database 104. In one embodiment, healthcare management software system 106 checks to see if the database integrity information 111 matches the integrity information 108 as the integrity test. Assuming patient database 104 passes the integrity test, a pop-up window 360 is displayed as part of user interface 300. Pop-up window 360 includes a textual label 362 indicating that patient database 104 includes the predefined data which is the database integrity information. Pop-up window 360 also includes textual labels 364 and 366 which indicate that patient database 104 has also passed two additional tests. The test corresponding to textual label 364 checks patient database 104 to make sure that patient database 104 has the correct database structure. In one embodiment, the correct database structure test checks to determine if all of the required database tables and database objects are contained in the patient database 104. The test corresponding to textual label 366 checks patient database 104 to make sure that patient database 104 has sufficient storage capacity for additional physiological data 110.

Although the invention has been described in detail with reference to certain preferred embodiments, variations and modifications exist within the spirit and scope of the invention as described and defined in the following claims.

The invention claimed is:

1. A method of checking the integrity of a database containing both physiological information and database integrity information, the database being accessible by a healthcare management software system, the method including the steps of:

providing a computer readable medium including installation software which installs a version of a healthcare management software system,
the installation software being able to install a first version of the healthcare management software system including a healthcare management software, a first database having physiological information and being accessible by the healthcare management software and a first database integrity information including at least one value utilized by the healthcare management software in determining information relating to physiological information to present with an output device, and a first file stored separate from the first database containing a first integrity information including at least one value utilized by the healthcare management software in determining information relating to the physiological information to present with the output device, the installation software also being able to install a second version of the healthcare management software system including a healthcare management software, a second database having a second database integrity information, and a second file containing a second integrity information;

receiving a request to perform the first installation;

installing the first version of the healthcare management software system; and determining an integrity of the first database through a comparison of the at least one value of the first database integrity information with the at least one value of the first integrity information;

wherein the step of determining is performed prior to the healthcare management software reading the physiological information in the first database.

2. The method of claim 1, wherein the at least one value of the first integrity information is a conversion quantity for the physiological information contained in the first database.

3. The method of claim 1, wherein the at least one value of the first integrity information includes data used by the healthcare management software in determining information to present with the output device.

4. The method of claim 1, wherein the at least one value of the first integrity information includes data not used by the healthcare management software in determining information to present with the output device, the data not used including at least one of a medical device key and a user identification code.

5. The method of claim 1 further including the step of installing the second version of the healthcare management software system, wherein the healthcare management software installed with the first version of the healthcare management software system is the same as the healthcare management software installed with the second version of the healthcare management software system.

6. The method of claim 1, wherein the first integrity information is included in a configuration file.

7. The method of claim 6, wherein the configuration file is an encrypted configuration file.

8. The method of claim 1, wherein the healthcare management software installed with the first version of the healthcare management software system at the step of installing is diabetes care software installed in a memory of a computing device.

9. The method of claim 8, wherein the healthcare management software communicates with a blood glucose meter and receives the physiological information included in the first database from the blood glucose meter.

10. The method of claim 1 further including the step of displaying the physiological information on a display following the step of determining.

11. The method of claim 1, wherein the first database integrity information matches the first integrity information and the second database integrity information matches the second integrity information.

12. A non-transitory computer readable medium having computer-executable instructions, the computer executable instructions including an installation software which installs a version of a healthcare management software system, the installation software being able to install a first version of the healthcare management software system including a healthcare management software, a first database having physiological information and being accessible by the healthcare management software and a first database integrity information including at least one value utilized by the healthcare management software in determining information relating to the physiological information to present with an output device, and a first file stored separate from the first database containing a first integrity information including at least one value utilized by the healthcare management software in determining information relating to the physiological information to present with the output device, the installation software also being able to install a second version of the healthcare management software system including a healthcare management software, a second database having a second database integrity information, and a second file containing a second integrity information;

wherein the healthcare management software installed with the first version of the healthcare management software system includes a plurality of computer-executable instructions capable of determining an integrity of the first database through a comparison of the at least one value of the first database integrity information with the at least one value of the first integrity information.

13. The computer readable medium of claim 12, wherein the first integrity information matches the first database integrity information and the second integrity information matches the second database integrity information.

14. The computer readable medium of claim 12, wherein the at least one value of the first integrity information is a conversion quantity for the physiological information contained in the first database.

15. The computer readable medium of claim 12, wherein the at least one value of the first integrity information includes data used by healthcare management software system in determining information to present with the output device.

16. The computer readable medium of claim 12, wherein the healthcare management software installed with the first version of the healthcare management software system is able to receive the physiological information from a blood glucose meter.

17. A system for verifying the integrity of a database comprising patient data, the system including:

a computing device having a processor and a display;

a computer readable memory accessible by the processor of the computing device, the memory including an installation software program comprising a plurality of instructions executable by the processor, the plurality of instructions when interpreted by the processor cause the processor to perform the steps of:

installing a first configuration of a healthcare management software system in the memory of the computing device, the first configuration including healthcare management software, a first database comprising physiological information accessible by the healthcare management software and a first database integrity information including at least one value utilized by the healthcare management software in determining information relating to the physiological information to display with the display, and a first file stored separate from the first database comprising first integrity information including at least one value utilized by the healthcare management software in determining information relating to the physiological information to display with the display, and installing a second configuration of the healthcare software system in a computer readable memory, the second configuration including healthcare management software, a second database comprising second database integrity information, and a second file comprising second integrity information, wherein the healthcare management software of the first configuration determines an integrity of the first database through a comparison of the at least one value of the first database integrity information with the at least one value of the first integrity information of the first file and the healthcare management software of the second configuration determines an integrity of the second database through a comparison of the second database integrity information with the second integrity information of the second file.

* * * * *